US007067258B2

(12) United States Patent
Esser et al.

(10) Patent No.: US 7,067,258 B2
(45) Date of Patent: Jun. 27, 2006

(54) HUMAN PAPILLOMAVIRUS MULTIPLEXED ASSAY

(75) Inventors: Mark T. Esser, Collegeville, PA (US); David W. Opalka, Hatfield, PA (US); Victor Goetz, Skillman, NJ (US); James E. Drummond, Harleysville, PA (US); Michael W. Washabaugh, Lower Gwynedd, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/513,088

(22) PCT Filed: Apr. 25, 2003

(86) PCT No.: PCT/US03/12913

§ 371 (c)(1),
(2), (4) Date: Oct. 29, 2004

(87) PCT Pub. No.: WO03/093511

PCT Pub. Date: Nov. 13, 2003

(65) Prior Publication Data

US 2005/0147961 A1 Jul. 7, 2005

Related U.S. Application Data

(60) Provisional application No. 60/376,721, filed on Apr. 30, 2002.

(51) Int. Cl.
*C12Q 1/68* (2006.01)
(52) U.S. Cl. .............................. 435/6; 435/7.1; 435/345
(58) Field of Classification Search .................... 435/6, 435/7.1, 345
See application file for complete search history.

(56) References Cited

U.S. PATENT DOCUMENTS 5,981,180 A 11/1999 Chandler et al.

FOREIGN PATENT DOCUMENTS

WO WO 01/13120 2/2001

OTHER PUBLICATIONS

Smith, et al., "A Rapid, Sensitive, Multiplexed Assay for Detection of Viral Nucleic Acids Using the FlowMetrix System", Clinical Chemistry, vol. 44, No. 9, pp. 2054-2056 (1998).

Fulton, et al., "Advanced multiplexed analysis with the FlowMetrix system", Clinical Chemistry, vol. 43, No. 9, pp. 1749-1756 (1997).
Martins, "Development of Internal Controls for the Luminex Instrument as Part of a Multiplex Seven-Analyte Viral Respiratory Antibody Profile", Clinical and Diagnostic Laboratory Immunology, vol. 9, No. 1 pp. 41-45 (2002).
Christensen, et al., "Monoclonal Antibodies to HPV-6 L1 Virus-like Particles Identify Conformational and Linear Neutralizing Epitopes on HPV-11 in Addition to Type-Specific Epitopes on HPV-6", Virology, vol. 224, pp. 477-487 (1996).
Giroglou, et al., "Immunological analyses of human papillomavirus capsids", Vaccine, vol. 19, pp. 1783-1793 (2001).
Yeager, et al., "Neutralization of Human Papillomavirus (HPV) Pseudovirions: A Novel and Efficient Approach to Detect and Characterize HPV Neutralizing Antibodies", Virology, vol. 278, pp. 570-577 (2000).
Brown, et al., "Neutralization of Human Papillomavirus Type 11 (HPV-11) by Serum from Women Vaccinated with Yeast-Derived HPV-11 L1 Virus-like Particles: Correlation with Competitive Radioimmunoassay Titer", The Journal of Infectious Diseases, vol. 184, pp. 1183-1186 (2001).
Vignali, "Multiplexed particle-based flow cytometric assays", Journal of Immunological Methods, vol. 243, pp. 243-255 (2000).
Bellisario, et al., "Simultaneous measurement of antibodies to three HIV-1 antigens in newborn dried blood-spot specimens using a multiplexed microsphere-based immunoassay", Early Human Development, vol. 64, pp. 21-25 (2001).
Bryan, et al., "Human Papillomavirus Type 11 Neutralization in the Athymic Mouse Xenograft System: Correlation With Virus-Like Particle IgC Concentration", Journal of Medical Virology, vol. 53, pp. 185-188 (1997).

(Continued)

*Primary Examiner*—Ali R. Salimi
(74) *Attorney, Agent, or Firm*—Alysia A. Finnegan; Joanne M. Giesser

(57) ABSTRACT

The present invention relates to an immunoassay for simultaneously measuring the presence of antibodies to a plurality of HPV types that utilizes particle-based flow cytometric analysis. The presence and/or titre of neutralizing antibodies in a test sample are determined in a competitive format, where known, type-specific, fluorescently labeled neutralizing monoclonal antibodies compete with antibodies within a test sample for binding to conformationally sensitive, neutralizing epitopes on specific HPV-VLPs. The invention also provides a microsphere complex comprising a microsphere coupled to an HPV VLP.

14 Claims, 11 Drawing Sheets

OTHER PUBLICATIONS

Krieder, et al., "Morphological transformation *in vivo* of human uterine cervix with papillomavirus from condylomata acuminata", Nature, vol. 317, No. 6038, pp. 639-341 (1985).

Roden, et al., "In Vitro Generation and Type-Specific Neutralization of a Human Papillomavirus Type 16 Virion Pseudotype", Journal of Virology, vol. 70, No. 9, pp. 5875-5883 (1996).

Palker, et al., "Antibody, cytokine and cytotoxic T lymphocyte responses in chimpanzees immunized with human papillomavirus virus-like particles", Vaccine, vol.19, pp. 3733-3743 (2001).

Wideroff et al., "Evaluation of Seroreactivity to Human Papillomavirus Type 16 Virus-like Particles in an Incident Case-Control Study of Cervical Neoplasia", The Journal of Infectious Diseases, vol. 172, pp. 1425-1430 (1995).

Nardelli-Haefliger, et al., "Mucosal but not Parenteral Immunization with Purified Human Papillomavirus Type 16 Virus-Like Particles Induces Neutralizing Titers of Antibodies throughout the Estrous Cycle of Mice", Journal of Virology, vol. 73, No. 11, pp. 9609-9613 (1999).

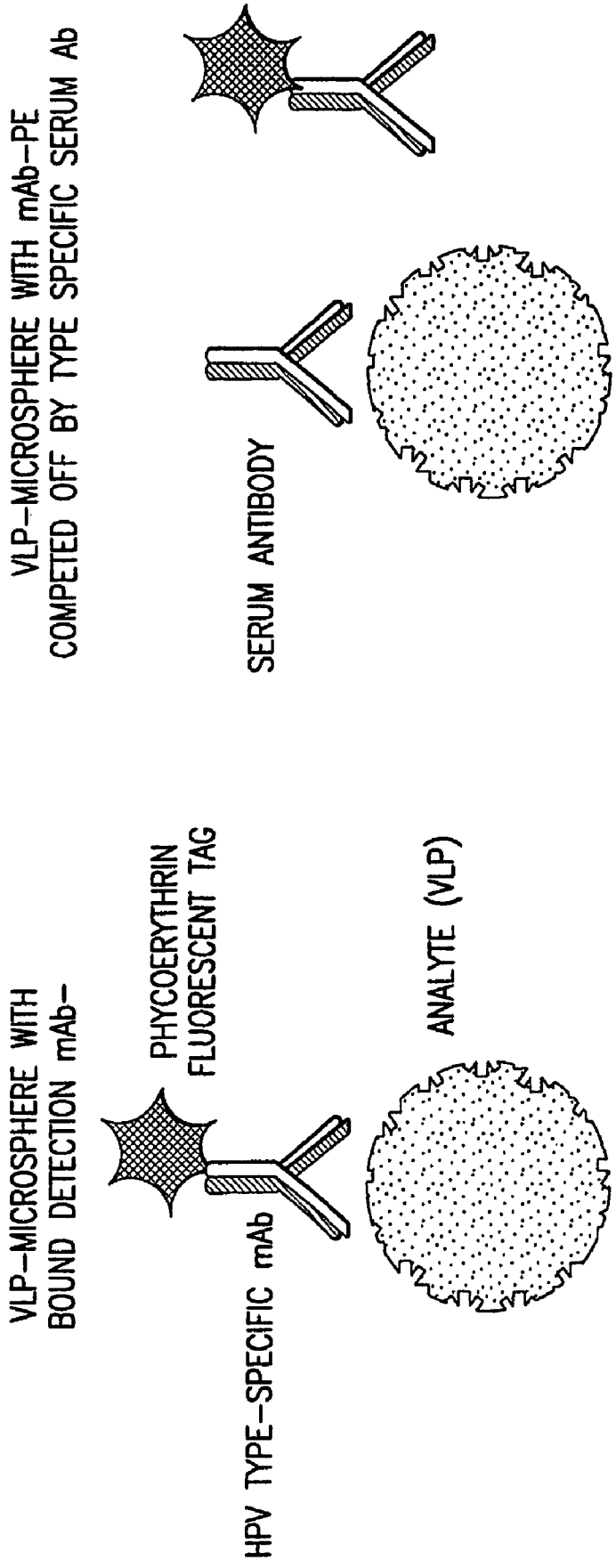

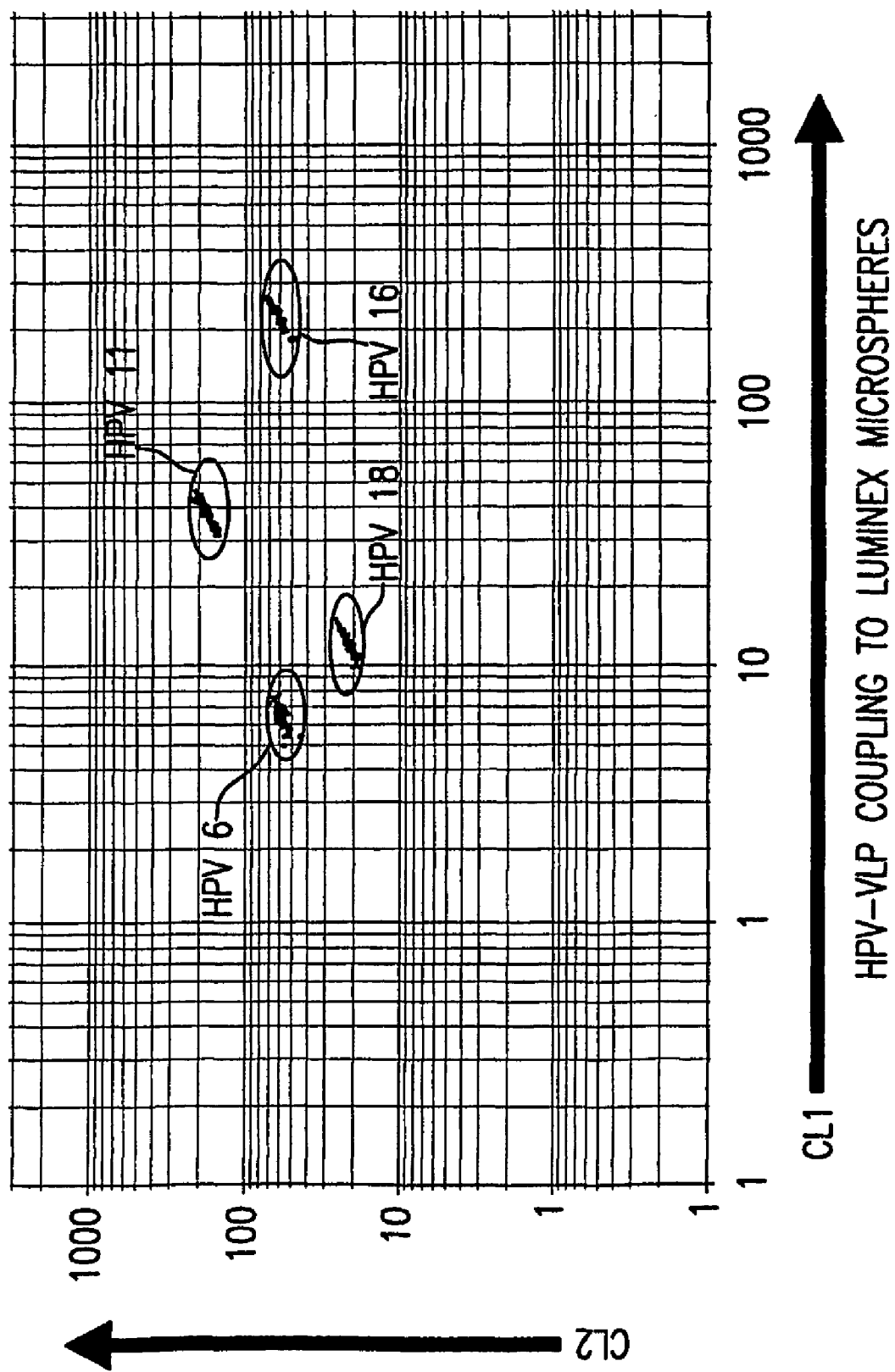

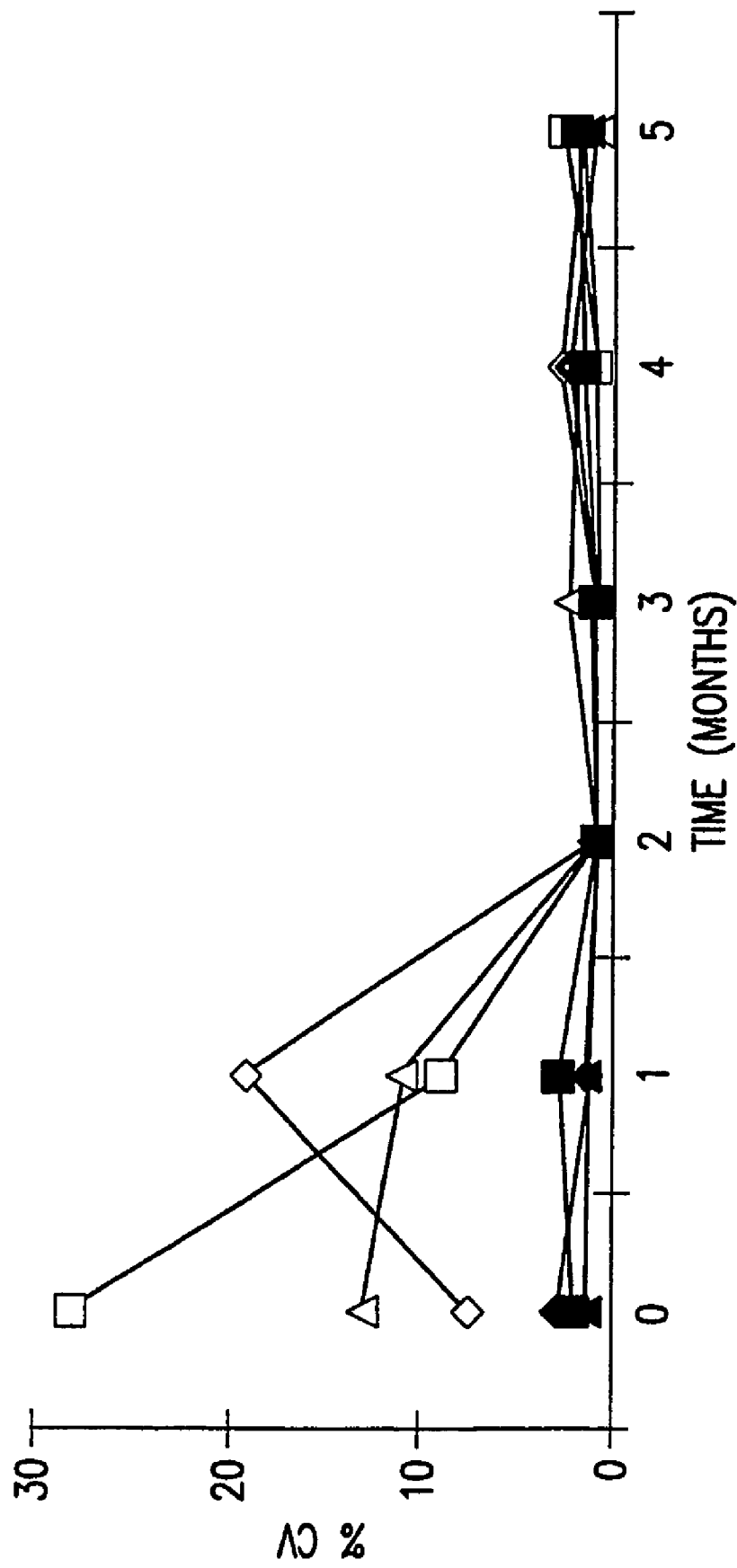

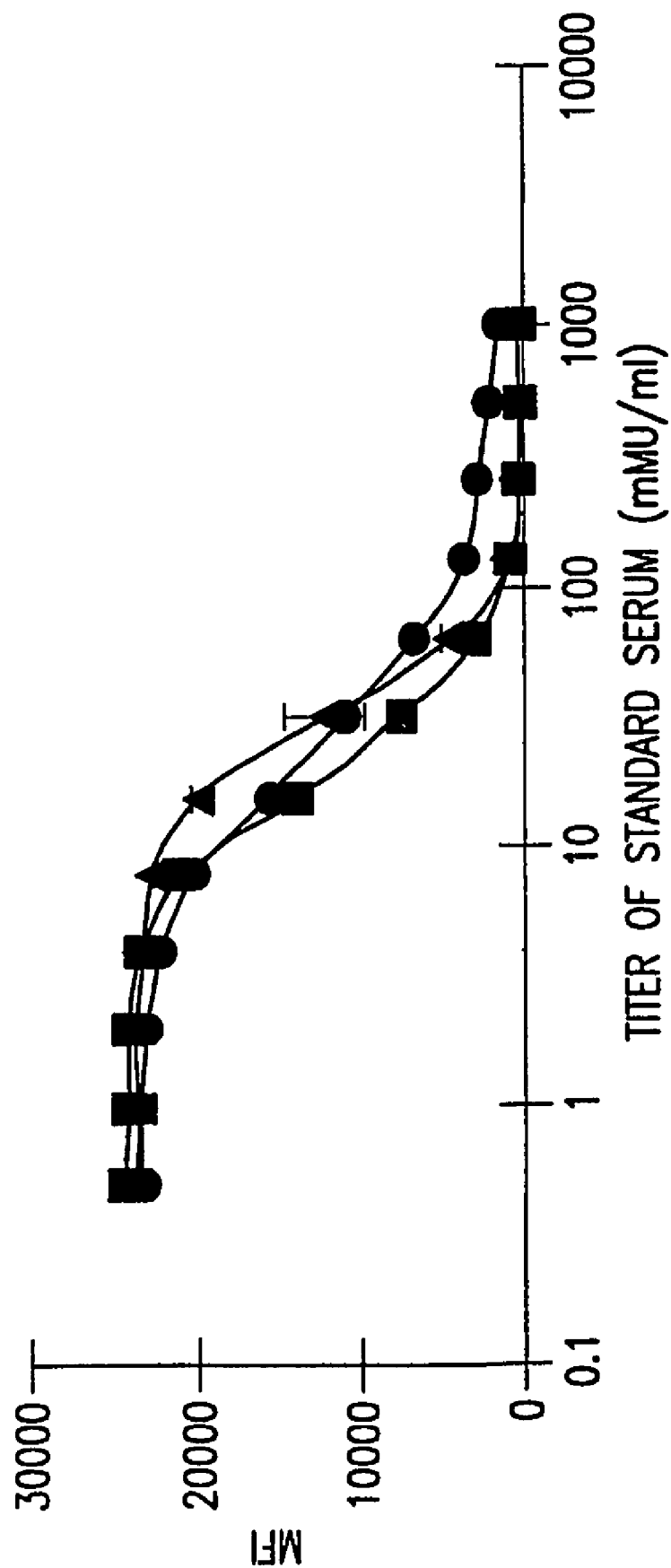

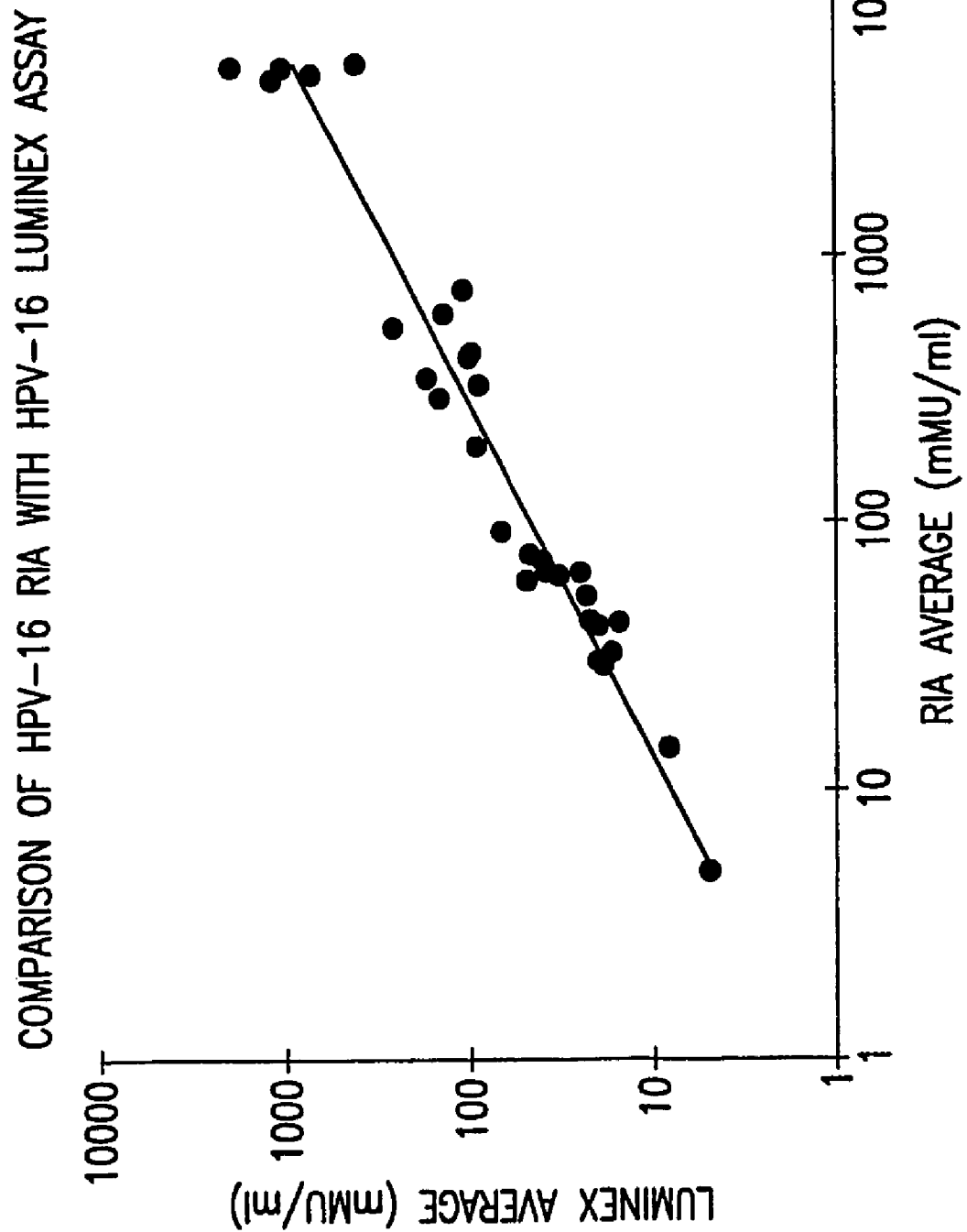

COMPETITIVE HPV RIA AND MULTIPLEX LUMINEX IMMUNOASSAY LIMITS OF DETECTION AND QUANTITATION.

| | HPV-6 | | HPV-11 | | HPV-16 | | HPV-18 | |
|---|---|---|---|---|---|---|---|---|
| | RIA | LUMINEX | RIA | LUMINEX | RIA | LUMINEX | RIA | LUMINEX |
| LIMIT OF DETECTION | 2.7 | 0.8 | 2.7 | 1.0 | 0.4 | 1.6 | 3.9 | 5.3 |
| LOWER LIMIT OF QUANTITATION | 8.0 | 1.2 | 13.0 | 9.8 | 6.0 | 4.5 | 13.0 | 11.3 |
| UPPER LIMIT OF QUANTITATION | 83.0 | 54.8 | 130.0 | 365.6 | 130.0 | 476.5 | 130.0 | 203.0 |

FIG.8

HUMAN PAPILLOMAVIRUS MULTIPLEXED ASSAY

This application is a 371 of PCT/US03/12913, international filing date of Apr. 25, 2003, which claims priority to U.S. Ser. No. 60/376,721, filed Apr. 30, 2002, now expired.

FIELD OF THE INVENTION

The present invention relates generally to the field of human papillomaviruses (HPV); particularly to methods for detecting the presence of HPV antibodies in clinical samples. More specifically, it relates to a multiplex competitive immunoassay, wherein antibodies specific to a plurality of HPV types are simultaneously detected and quantified.

BACKGROUND OF THE INVENTION

More than 80 types of human papillomavirus (HPV) have been described, many of which are associated with a wide variety of biological phenotypes, from benign proliferative warts to malignant carcinomas (for review, see McMurray et al., *Int. J. Exp. Pathol.* 82(1): 15–33 (2001)). HPV6 and HPV11 are the types most commonly associated with benign warts, whereas HPV16 and HPV18 are the high-risk types most frequently associated with malignant lesions. More than 90% of cervical carcinomas are associated with infections of HPV16, HPV18 or the less prevalent oncogenic types HPV31, -33, -45, -52 and -58 (Schiffman et al., *J. Natl. Cancer Inst.* 85(12): 958–64 (1993)). The observation that HPV DNA is detected in more than 90% of cervical cancers provides strong epidemiological evidence that HPVs cause cervical carcinoma (see Bosch et al., *J. Natl. Cancer Inst.* 87(11): 796–802 (1995)).

An effective vaccine against HPV is needed to prevent the development of cervical dysplasias and carcinomas and their associated morbidity and mortality. Vaccines to both the low risk and high risk HPV types are currently being tested in clinical trials. The ability to determine the presence of HPV type-specific antibodies to several HPV types in clinical samples would be useful for both monitoring the efficacy of prospective vaccines and for natural history infection studies.

Several different methods have been developed to quantify neutralizing antibodies to HPVs, including in vivo neutralization assays, in vitro pseudo-neutralization assays, competitive radioimmunoassays (cRIAs), and enzyme-linked immunosorbent assays (ELISAs). However, each of these techniques possesses one or more limitations that preclude testing large numbers of patient sera for use in large vaccine clinical trials and natural history studies.

The most common technique for measuring neutralizing HPV antibody titers is the athymic mouse xenograft system (Bryan et al., *J. Med. Virol.* 53(3): 185–88 (1997); Kreider et al., *Nature* 317(6038): 639–41 (1998). In this assay, sera from individuals is mixed with infectious HPV and added to foreskin tissue, which is then implanted under the renal capsule of athymic mice. The implants are monitored for histological changes and for HPV DNA by in situ hybridization. Because such histological changes can take several months to develop, this method is unsuitable for high throughput analysis.

Due to the technical difficulties in testing a large number of sera in the athymic mouse xenograft system, several complementary assays have been developed to measure neutralizing and non-neutralizing antibody titers. These include in vitro pseudo-neutralization assays (Bryan et al., supra; Roden et al., *J. Virol.* 70(9): 5875–83 (1996)), competitive RIAs (Palker et al., *Vaccine* 19(27): 3733–43 (2001)) and virus like particle (VLP)-based ELISAs (Wideroff et al., *J. Infect. Dis.* 172(6): 1425–30 (1995)). Studies have shown that the pseudo-neutralization assay can be 20- to 30-fold less sensitive than HPV-VLP ELISAs (Nardelli-Haefliger et al., *J. Virol.*, 73(11): 9609–13 (1999)) and up to a 100-fold less sensitive than a competitive RIA (Palker et al., supra). However, because ELISA-based assays can only detect one analyte at a time, this technique is impractical for analyzing large numbers of clinical samples where detecting and quantifying antibody titre to several HPV types is desirable.

Recently, methods have been developed to simultaneously measure multiple analytes using particle-based flow cytometric assays. This approach has been used to measure numerous types of soluble analytes, including antibodies specific to various antigens, and to quantify the cell surface expression of various receptors (for review, see Vignali, *J. Immunol. Methods* 243: 243–255 (2000)). Schlottman and colleagues used this method in pneumococcal vaccine studies to measure the antibody response to a pneumoconjugate vaccine (Martins, *Clin Diagn Lab Immnwol:* 9(1): 41–45 (2002)). Bellisario and colleagues developed a particle-based flow cytometric assay to simultaneously measure antibodies to HIV-1 antigens p24, gp160 and gp120 in newborn dried blood-spot specimens (*Early Human Devel.* 64: 21–25 (2001)). Both of these studies utilized simple capture-type assays where the desired analytes are directly detected in a sample.

Despite the development of the immunoassays described above, it would be advantageous to develop an assay to measure HPV type-specific antibodies to neutralizing epitopes that is highly sensitive and reproducible, and that requires reduced man-hours compared to methods disclosed in the art. An immunoassay that measures HPV type-specific antibodies to several HPV types simultaneously would be preferable to a single serological assay, which requires serial experimentation.

SUMMARY OF THE INVENTION

The present invention relates to an immunoassay for detecting the presence of antibodies to a plurality of HPV types that utilizes particle-based flow cytometric analysis. The presence and/or titre of neutralizing antibodies are determined in a competitive format, where known, type-specific, detectably-tagged neutralizing antibodies compete with antibodies within a test sample for binding to conformationally sensitive, neutralizing epitopes on the HPV VLPs.

More specifically, the present invention relates to a competitive immunoassay for detecting antibodies to neutralizing epitopes on at least one human papillomavirus (HPV) type in a sample from a subject comprising: (a) providing at least one microsphere set, wherein each set comprises: (i) a unique sorting characteristic and (ii) a microsphere complex comprising a microsphere coupled to a unique HPV virus-like particle (VLP) type and a detectably tagged monoclonal antibody which binds to the VLP; (b) contacting the at least one microsphere set with the sample so that any antibodies within the sample can bind to the VLP; and (c) for each microsphere set, determining either: (i) the amount of detectably tagged monoclonal antibodies that bind to the VLP; or (ii) the amount of detectably tagged monoclonal antibodies that do not bind to the VLP.

The present invention further relates to a competitive immunoassay for detecting neutralizing antibodies to a plurality of HPV types in a sample from a subject wherein Luminex Laboratory MultiAnalyte Profiling Technology (LabMAP®, Luminex Corp., Austin, Tex.) is used in conjunction with the LUMINEX100™ desktop analyzer to simultaneously measure antibodies to a plurality of HPV types from a single serum sample. In one embodiment of the invention, yeast-derived VLPs are used that have been coupled to a plurality of distinct fluorescent Luminex microspheres. The type specific HPV-VLP antibody (Ab) responses are associated with specific Luminex microspheres that are identified by their distinct red and infrared fluorescent dye spectral properties on the LUMENX100™ (Fulton et al., *Clin. Chem.* 43(9): 1749–56 (1997)). Neutralizing antibody titers are determined in a competitive format, where known, HPV-type-specific, phycoerythrin (PE)-labeled, neutralizing detection antibodies compete with patient serum antibodies for binding to conformationally sensitive, neutralizing epitopes on the VLPs. The method of the present invention accurately and precisely measures HPV type-specific antibodies simultaneously in human serum.

The present invention also relates to a competitive immunoassay for detecting antibodies to neutralizing epitopes on human papillomavirus (HPV) types-6, -11, -16 and -18 in a sample of serum from a subject comprising: (a) providing four fluorescent microsphere sets, wherein each of the four microsphere sets comprises: (i) a unique spectral property; and (ii) a microsphere complex comprising a microsphere coupled to a unique HPV VLP type and a monoclonal antibody that binds to the VLP; wherein the monoclonal antibody is labeled with a phycoerythrin reporter molecule; wherein a first microsphere set is coupled to an HPV6 VLP, a second microsphere set is coupled to an HPV11 VLP, a third microsphere set is coupled to an HPV16 VLP, and a fourth microsphere set is coupled to an HPV18 VLP; (b) contacting the four microsphere sets with the sample of serum so that any antibodies within the sample can bind to the VLPs; (c) for each microsphere set, determining either (i) the amount of phycoerythrin-labeled monoclonal antibodies that bind to the VLP; or (ii) the amount of phycoerythrin-labelled monoclonal antibodies that do not bind to the VLP; wherein inhibition of binding of the detection antibodies indicates that antibodies are present in the sample of serum that are specific to HPV-6, -11, -16 or -18.

The invention also relates to a microsphere complex comprising a microsphere coupled to an HPV virus-like particle (VLP). In a preferred embodiment of the invention, the microsphere complex further comprises a detectably tagged monoclonal antibody bound to the VLP.

As used throughout the specification and in the appended claims, the singular forms "a", "an", and "the" include plural reference unless the context clearly dictates otherwise.

As used throughout the specification and appended claims, the following definitions and abbreviations apply:

"Plurality" means two or more.

"HPV" means human papillomavirus. "HPV" is a general term used to refer to any subtype of HPV, whether currently known or subsequently described.

"Microsphere" refers to a small particle that can be covalently attached or otherwise coupled to a specific HPV-VLP for use in the methods of the present invention. The terms microsphere, particle, microparticle, bead or microbead are used interchangeably and bear equivalent meanings.

"Microsphere set" refers to a plurality of microspheres that share a defining "unique sorting characteristic" that allows the microspheres to be identified as part of a set and distinguished from microspheres that comprise a different microsphere set. The "unique sorting characteristic" can be detected, for example, by a flow cytometer, and serves as the basis for distinguishing one microsphere set from another. An exemplary "unique sorting characteristic" is the size of the bead. If bead size is chosen as the unique sorting characteristic, all beads within a specific microsphere set should be relatively the same size and all beads not part of that specific microsphere set should be of a different size.

Alternatively, microsphere sets may be labeled with differing proportions of two or more fluorescent dyes, allowing the emission wavelengths and fluorescence intensities to serve as the unique sorting characteristic. For instance, in EXAMPLE 3, HPV VLP 6, 11, 16 and 18 were each coupled to unique microsphere sets provided by the Luminex Corp. (Austin, Tex.). In developing distinguishable, unique microsphere sets, Luminex internally color-coded populations of beads by varying the proportions of two fluorescent dyes. Use of unique microsphere sets to detect different analytes, i.e. antibodies in a sample, permits analytes to be separated by an instrument capable of detecting the unique sorting characteristic. In the case of fluorescently-labeled microsphere sets, for example, beads from one microsphere set can be sorted or separated from beads belonging to another set and quantified by a flow cytometer.

In the methods of the present invention, each microsphere set comprises a plurality of microspheres coupled to a "unique HPV VLP type," meaning that each microsphere set comprises a plurality of microspheres that are linked to a specific HPV VLP type that is different relative to the HPV VLP types linked to a different microsphere set. A single microsphere set, however, comprises a single HPV VLP type.

"Microsphere complex," which is used interchangeably herein with the terms "VLP-microsphere(s)," and "VLP-microsphere complex" refers to a microsphere coupled to an HPV VLP. For example, a microsphere complex may comprise a Luminex bead 138, provided commercially by Luminex for use in conjunction with LabMAP® technology, coupled to a VLP derived from HPV 16, as in EXAMPLE 3. Alternatively, one of skill in the art may substitute any bead or microparticle known in the art or subsequently identified, coupled to an HPV VLP derived from any HPV type. A microsphere complex may further comprise a detectably tagged monoclonal antibody that binds to the VLP.

"VLP" or "VLPs" mean(s) virus-like particle or virus-like particles. Virus-like particles can self-assemble when L1, the major capsid protein of human and animal papillomaviruses, is expressed in yeast, insect cells, mammalian cells or bacteria (for review, see Schiller and Roden, in *Papillomavirus Reviews: Current Research on Papillomaviruses;* Lacey, ed. Leeds, UK: Leeds Medical Information, pp 101–12 (1996)). Morphologically indistinct HPV VLPs can also be produced by expressing a combination of the L1 and L2 capsid proteins. VLPs are composed of 72 pentamers of L1 in a T=7 icosahedral structure (Baker et al., *Bioplzys. J.* 60(6): 1445–56 (1991)).

VLPs are morphologically similar to authentic virions and are capable of inducing high titres of neutralizing antibodies upon administration into an animal. Immunization of rabbits (Breitburd et al., *J. Virol.* 69(6): 3959–63 (1995)) and dogs (Suzich et al., *Proc. Natl. Acad. Sci.* USA 92(25): 11553–57 (1995)) with VLPs was shown to both induce neutralizing antibodies and protect against experimental papillomavirus infection. However, because the VLPs do not contain the potentially oncogenic viral genome and can self-assemble from a single gene, they present a safe alternative to use of live virus in HPV vaccine development (for review, see Schiller and Hidesheim, *J. Clin. Virol.* 19: 67–74 (2000)).

"PE" refers to the fluorescent label phycoerythrin.

"CV" or "%CV" refers to the coefficient of variation.

"MFI" refers to median fluorescent intensity.

"Ab" and "mAb" stand for "antibody" and "monoclonal antibody," respectively.

"Detection antibody" or "detection Ab" refers to a detectably tagged HPV type-specific antibody, which is bound to a microsphere complex for use in the competitive assays of the present invention. Detection antibodies are bound to type-specific VLPs, which make up a portion of a microsphere complex. The competitive immunoassays of the present invention measure titers of polyclonal Abs in patient samples that are capable of displacing binding of detection antibodies to conformationally sensitive, neutralizing epitopes on the respective VLPS. The fluorescent signal from the bound HPV-specific detection Abs is inversely proportional to the patient's neutralizing Ab titer.

"Reporter molecule," also known as "fluorescent tag," "fluorescent reporter molecule," "reporter fluorochrome," or "detectable tag," refers to a fluorescent agent which associates with, establishes the presence of, or allows the quantification of a particular antibody. A reporter molecule can be, for example, phycoerythrin.

As used herein, "CL1" and "CL2" refer to classification 1 and classification 2, respectively. In an exemplary embodiment of the invention, CL1 refers to the emission spectra from Luminex microspheres at 658 nm and CL2 refers to the emission spectra at 712 nm. The Luminex instrument measures the two classification wavelengths to determine which microsphere is being analyzed.

"cRIA" refers to a competitive radioimmunoassay.

BRIEF DESCRIPTION OF THE DRAWINGS

FIG. 1 shows an exemplary HPV-Luminex multiplex competitive immunoassay. Panel A presents a schematic diagram of the assay design for the HPV-Luminex immunoassay. This immunoassay quantitatively measures the ability of HPV type-specific antibodies in patient sera to prevent binding of phycoerythrin-labeled, HPV type-specific detection monoclonal antibodies (mAbs). The fluorescent signal from bound HPV-specific detection mAbs is inversely proportional to the patient's antibody titer to HPV type-specific neutralizing epitopes on the respective VLP. Panel B shows a schematic diagram of an HPV VLP microsphere complex where the PE-tagged mAb is competed off by type-specific HPV Ab found in patient serum.

FIG. 2 shows the designation of HPV-VLP types to distinct Luminex microspheres (see EXAMPLE 3). Each HPV-VLP was coupled to a specific Luminex microsphere population with discrete classification 1 (CL1) 658 nm and classification 2 (CL2) 712 nm spectral properties to allow separation by automatic gating (ovals indicate gates). VLP-6 was coupled to microsphere 132, VLP-11 to microsphere 153, VLP-16 to microsphere 138 and VLP-18 to microsphere 118.

FIG. 3 shows the stability of HPV-VLP-16 coupled to Luminex microspheres. The stability of HPV types-6, -11, -16 and -18 VLPs coupled to Luminex microspheres was examined for a period of 6 months. VLP-microspheres were stored at 4° C., in the dark in either PBS (represented by diamonds), Column A buffer (represented by triangles) or a Histidine buffer (represented by squares) in the presence or absence of 1% BSA. Open symbols represent storage in the absence of BSA and closed symbols represent storage conditions in the presence of 1% BSA, respectively. Representative data for VLP-16 coupled to microsphere 138 is shown. The MFI for 32 replicate samples was averaged and the % CV determined. The % CV was less than 10% for all four HPV-VLP types stored in buffers containing 1% BSA.

FIG. 5 depicts the effect of serum and different assay buffers on the HPV-Luminex assay (see EXAMPLE 5). A standard reference serum from a VLP-11 immunized African green monkey was analyzed in various assay diluent buffers. Two-fold serial dilutions of a stock reference standard into HPV negative normal human serum (NHS) was performed to create a twelve point standard curve. The standard reference serum was analyzed in PBS/1% BSA (represented by circles) or HPV negative NHS, with a wash step that included 3 rinses with PBS/1% BSA in a filter plate (represented by triangles) or without (represented by squares). Error bars represent the standard deviation of duplicate samples.

FIG. 7 shows a comparison of titers determined in an HPV-16 cRIA assay with titers from a multiplex competitive Luminex immunoassay (see EXAMPLE 7). HPV type specific antibody titers (mMU/mL) for 45 samples were determined by cRLA and Luminex immunoassays. Antibody titers were determined for 15 HPV negative, 15 low, 10 medium and 5 high titer serum samples. The cRIA and Luminex assays were both performed in duplicate and the average of the duplicate runs were compared for intra-assay precision and inter-assay accuracy. Average mMU/mL values for the HPV-16 cRIA and Luminex assays are shown.

FIG. 8 shows a comparison of the limits of detection and quantitation for the competitive RIAs and the Luminex multiplex immunoassays in milli-Merck units/mL for HPV-6, -11, -16 and -18 assays.

DETAILED DESCRIPTION OF THE INVENTION

Figure 4A:
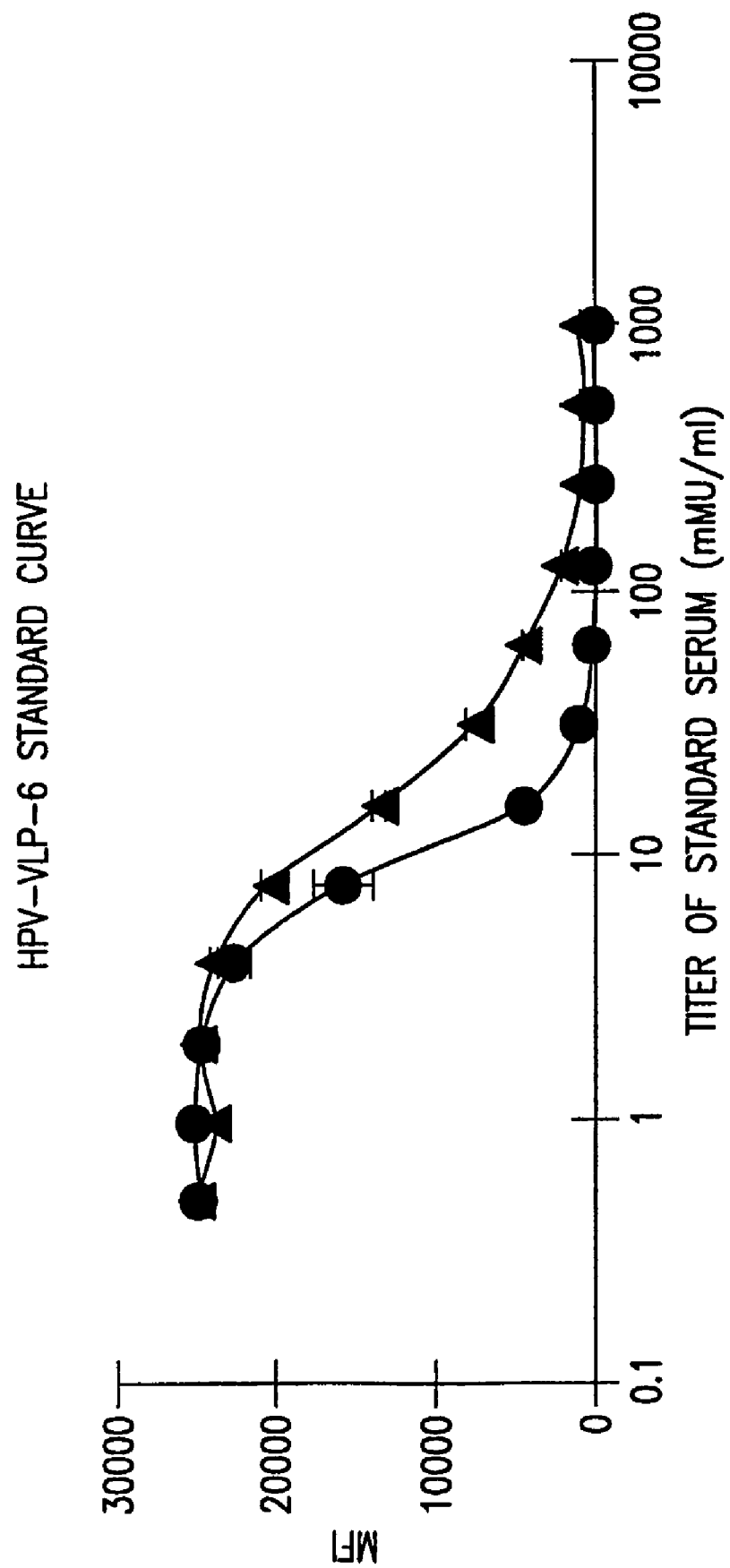
FIG. 4 shows simplex and multiplex standard curves for HPV types-6, -11, -16 and -18. Representative standard curves for a 12-point dilution series of a standard reference serum different African green monkey sera for HPV-VLP-6 (Panel A), HPV-VLP-11 (Panel B), and HPV-VLP-18 (Panel D) and chimpanzee sera for HPV-VLP-16 (Panel C). Simplex curves depict results from a single standard serum run in the assay with only one VLP-microsphere type present (represented by triangles) and multiplex curves depict a quadrivalent standard with all four VLP-microspheres present in a single well (represented by circles). Error bars represent the standard deviation for duplicate samples.

A common goal for all vaccine programs is to identify clinically relevant correlates of protection. Specifically, laboratory parameter(s) that have been shown to be associated with protection from clinical disease must be identified.

For many infectious diseases, neutralization antibody (Ab) assays are used to assess the immunogenicity of prophylactic vaccines.

Accordingly, the present invention relates to a competitive immunoassay for detecting antibodies to neutralizing epitopes on at least one human papillomavirus (HPV) type in a sample from a subject comprising: (a) providing at least one microsphere set, wherein each set comprises: (i) a unique sorting characteristic and (ii) a microsphere complex comprising a microsphere coupled to a unique UPV virus-like particle (VLP) type and a detectably tagged monoclonal antibody that binds to the VLP; (b) contacting the at least one microsphere set with the sample so that any antibodies within the sample can bind to the VLP; and (c) for each microsphere set, determining either (i) the amount of detectably tagged monoclonal antibodies that bind to the VLP; or (ii) the amount of detectably tagged monoclonal antibodies that do not bind to the VLP.

In the methods of the present invention, inhibition of binding or a reduction in the amount of binding of the detectably tagged monoclonal antibodies to the HPV type-specific VLPs indicates that antibodies to HPV type-specific neutralizing epitopes are present in the sample of the subject which are specific to that HPV type. The fluorescent signal from the bound BHV-specific, detection m-Abs is inversely proportional to the subject's neutralizing antibody titer.

The methods of the present invention may be carried out with at least one microsphere set. One of skill in the art may vary the number of microsphere sets, depending on the number of HPV type-specific antibodies to be screened for in the patient or subject sample. Preferably, a plurality of microsphere sets is used to detect antibodies to a plurality of HPV-types within a sample concurrently.

By "concurrently" or "simultaneously," it is meant that the presence and/or titre of a plurality of HPV type-specific antibodies representing different HPV types present in a sample can be detected in a single experimental protocol. In other words, one of skill in the art can determine the presence and/or quantity of HPV antibodies to more than one HPV type with a single set of reagents in a single well of an assay plate. For example, the methods of the present invention allow one of skill in the art to simultaneously detect the presence of HPV6, -11, -16 and -18 antibodies in a test sample by mixing, in a single well of a 96-well plate, the appropriate reagents, the test sample, and microsphere sets designed to detect the HPV types of interest. In such a case, results can be obtained for HPV6, -11, -16 and -18 in a single experiment, without having to utilize four separate aliquots of the test sample or four different wells in the assay plate. Therefore, the methods of the present invention advantageously allow one of skill in the art to screen for antibodies to more than one HPV type in a sample without the serial experimentation required by prior art methods.

In a preferred embodiment of the invention, the competitive immunoassay described further comprises the step of quantifying the antibody titre specific to each of the plurality of HPV types in the sample from the subject.

In another embodiment of the invention, the competitive immunoassay further comprises the step of coupling a type-specific HPV VLP to each of the plurality of fluorescent microsphere sets.

Advantageously, the methods of the present invention allow the simultaneous detection of a plurality of HPV types of interest in a single sample, as discussed above. In addition to the flexibility to detect any combination of HPV types with the assay disclosed herein, the methods of the present invention also provide the ability to add other assays, such as viral load measurements or cytokine assays to the same test. The instant invention also allows one of skill in the art to easily quantify antibodies to a plurality of HPV types simultaneously with a single test sample, if desired.

The multiplex competitive immunoassays of the present invention are an improvement over prior art methods utilizing a simple capture assay format because capture assays to VLPs measure a combination of antibodies to both neutralizing and non-neutralizing epitopes, and potentially other antibodies to yeast derived proteins. The use of a competitive immunoassay, as in the methods of the present invention, ensures greater specificity and reproducibility. The competitive format also allows one to test samples at a high concentration to test for low titer HPV type-specific antibodies.

In addition, the novel methods of the present invention permit the HPV antibody status of a sample to be accurately and quickly determined with a smaller volume of sample compared to prior art methods. In an exemplary embodiment of the methods of the present invention, only 50 µl of serum from a subject was used to determine the presence of antibodies to several RPV types (see EXAMPLE 4). Since numerous HPV assays can be performed simultaneously with a single sample, the methods of the present invention save on labor, valuable reagents, such as pediatric serum, and consumables. Moreover, the present invention permits internal controls to be utilized in each sample to ensure specificity. The present invention is also advantageous in that it allows the detection of antibodies with non-radioactive substances, which is safer for laboratory personnel.

HPV types for use in the present invention may be any plurality of HPV types of interest, including any HPV types described in the art or those subsequently identified. For example, the HPV types may include, but are not limited to: HPV6, HPV11, HPV16, HPV18, HPV31, HPV33, HPV35, HPV39, HPV45, HPV51, HPV52, HPV55, HPV56, HPV58, HPV59, and HPV68.

The methods of the present invention may be adapted for monitoring the efficacy of prospective HPV vaccines, wherein the HPV types of interest would correlate with the HPV types included in a vaccine candidate in development. In such cases, the HPV types of interest may be those types associated with oncogenic or other undesirable phenotypes. Accordingly, an exemplary embodiment of the invention provides a plurality of HPV types wherein the HPV types comprise HPV6, HPV11, HPV16 and HPV18.

To this end, the present invention also relates to a competitive immunoassay for detecting antibodies to neutralizing epitopes on human papillomavirus (HPV) types-6, -11, -16 and -18 in a sample of serum from a subject comprising: (a) providing four fluorescent microsphere sets, wherein each of the four microsphere sets comprises: (i) a unique spectral property; and (ii) a microsphere complex comprising a microsphere coupled to a unique HPV VLP type and a monoclonal antibody that binds to the VLP; wherein the monoclonal antibody is labeled with a phycoerythrin reporter molecule; wherein a first microsphere set is coupled to an HPV6 VLP, a second microsphere set is coupled to an HPV11 VLP, a third microsphere set is coupled to an HPV16 VLP, and a fourth microsphere set is coupled to an HPV18 VLP; (b) contacting the four microsphere sets with the sample of serum so that any antibodies within the sample can bind to the VLPs; (c) for each microsphere set, determining either (i) the amount of phycoerythrin-labeled monoclonal antibodies that bind to the VLP; or (ii) the amount of phycoerythrin-labelled monoclonal antibodies that do not bind to the VLP; wherein inhibition of binding of the detection antibodies indicates that antibodies are present in the sample of serum that are specific to HPV-6, -11, -16 or -18.

HPV VLPs for use in the present invention may be produced ii vivo, in suitable host cells, e.g. mammalian and insect host cells, or may form spontaneously upon purification of recombinant L1 proteins. In an exemplary embodiment of the invention, the VLPs are purified from lysates of the yeast *Saccharomyces cerevisiae*.

The present invention relates to a method for determining the presence of HPV type-specific antibodies in a sample from a subject. One of skill in the art will recognize that any bodily fluid from the subject of interest that could contain neutralizing antibodies to HPV types could be used as a source of the sample for purposes of this invention. For example, samples for use in the methods of the present invention could be, but are not limited to, serum, plasma, whole blood, cerebral spinal fluid, bone marrow aspirates, lymph node suspensions or urine. In a preferred embodiment of the invention, the sample consists of serum from the subject.

Microspheres for use in the present invention may be any particle or bead to which HPV VLPs may be attached for use in particle-based flow cytometric analyses and are available commercially from several companies including the Luminex Corp. (Austin, Tex.), and Becton Dickinson (San Jose, Calif.). Microspheres preferably range in size from 0.01 to 100 μm in diameter, more preferably from about 1 μm to about 20 μm.

Microspheres within a single microsphere set are preferably about the same size. Beads from different microsphere sets may be of the same size or may vary in size so that their size may serve as a distinguishing parameter or unique sorting characteristic for use in the methods of the present invention. Microsphere sets comprising microspheres of about the same size may be distinguished based on another parameter, such as a unique spectral property, which may be detected by a flow cytometer.

Said microspheres may be constructed of any material to which VLPs may be attached for detection by the detection instrument. For example, acceptable materials for the construction of microspheres include but are not limited to: polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, or combinations thereof. In a preferred embodiment of the present invention, microspheres are constructed of polystyrene.

Microspheres may optionally comprise additional functional groups useful for attachment of analytical reactants, such as the VLPs of the present invention. Said functional groups may be, but are not limited to, carboxylates, esters, alcohols, carbamides, aldehydes, amines, sulfur oxides, nitrogen oxides, or halides. Microspheres comprising said functional groups are available commercially. For example, the Luminex Corporation provides carboxylated microspheres for use with their LabMAP® technology. Carboxylation of the microspheres permits the covalent coupling of the VLPs using straightforward chemical techniques.

Any characteristic or parameter capable of being detected and/or quantified by a flow cytometer or other detection instrument can provide a basis for particle selection or sorting by a detection instrument. Said parameters provide a means for distinguishing one VLP-microsphere set from another, and, therefore, populations of HPV VLPs within a sample can be separately detected and quantified. In a preferred embodiment of the invention, the "unique soiting characteristic" that defines the microsphere sets is a unique spectral property.

Any monoclonal antibody capable of binding to conformationally sensitive, neutralizing epitopes on any HPV VLP of interest may be used in the method of the present invention as a detection antibody. Several monoclonal antibodies that neutralize HPV viruses, as shown by in vivo neutralization assays and in vitro pseudo-neutralization assays, have been previously described in the art (see, e.g. Christensen et al., *Virology* 224(2): 477–86 (1996)).

In addition, one of skill in the art will realize that monoclonal antibodies for use in the present invention may be produced by methods known in the art using HPV VLPs, polypeptides, proteins or portions thereof as antigens. For example, monoclonal antibodies can be produced as described, in Harlow and Lane, *Antibodies: A Laboratory Manual* (Cold Spring Harbor Laboratory (1988)), which is incorporated herein by reference. HPV polypeptides for use as antigens can be naturally isolated or prepared synthetically (using commercially available synthesizers). Preferably, HPV VLPs are used as antigens to produce monoclonal antibodies for use in the present invention.

In a preferred embodiment of the invention, the H6.B10.5, H11.B2, H16.V5, and H18.J4 monoclonal antibodies are used as detection antibodies, which are specific to HPV6, HPV11, HPV16 and HPV18, respectively (see Christensen et al., Virology 224(2): 477–86 (1996); Christensen et al., J. Virol. 64(11): 5678–81 (1990); Christensen et al., Virology 223(1): 174–84 (1996); and Yeager et al., Virology 278(2): 570–77 (2000)).

Monoclonal detection antibodies to be used in the methods of the present invention can be labeled with any molecule capable of being detected by a flow cytometer or other detection instrument, hereinafter "reporter molecule". A reporter molecule, therefore, should be chosen which emits light within the range detectable by the instrument. Instruments for use in the present invention comprise a method of excitation, such as a laser, which have a known excitation wavelength that dictates the necessary emission wavelength of the reporter molecule. For example, the LUMINEX100™ (Luminex Corp., Austin, Tex.) detection instrument comprises an argon laser, which has an excitation wavelength of 532 nm. Based on this excitation wavelength, one of skill in the art choosing to use the LUMINEX 100™ for use in the present invention, must choose a reporter molecule which emits light at or near 575 nm. Varying the method of excitation, therefore, will allow the use of a greater variety of reporter molecules.

In a preferred embodiment of the invention, the monoclonal antibodies are labeled with a fluorescent reporter molecule. One of skill in the art will recognize that any fluorescent molecule capable of being detected and/or quantified by the detection instrument can be used as the reporter molecule to label the HPV type-specific mAbs for use in the methods of the present invention. As discussed above, the means of excitation and the detection means of the detection instrument will dictate the choice of available reporter molecules. Reporter molecules may include, but are not limited to the following: fluorescein isothiocyanate (FTTC), phycoerythrin (PE), cytofluor tangerine, Alexa™ 532 and Alexa™ 546 (Molecular Probes, Eugene, Oreg.), cyanine 3 (Cy3), cyanine 5 (Cy5), cyanine 5.5 (Cy5.5; Amersham Pharmacia Biotech, Piscataway, N.J.), lissamine rhodamine B, tetramethylrhodamine isothiocyanate (TRITC), sulforhodamine B, BODIPY-TMR-X (Molecular Probes), PBXL-1 (Martek Biosciences, Columbia, Md.), Texas red-avidin (Molecular Probes), streptavidin, C-phycocyanin, R-phycocyanine II, allophycocyanins (APC) such as APC-B, peridinin chlorophyll protein (PerCP), cascade blue, coumarin. Other fluorescent reporters that can be used in conjunction with the methods of the present invention are well known in the art (see, e.g., Shapiro, H. M., *Practical Flow Cytometry*, Third edition. New York: Wiley-Liss, 1995, which is herein incorporated by reference).

In a preferred embodiment of the novel method disclosed herein, the HPV type-specific detection mAbs are labeled with the fluorescent reporter molecule phycoerythrin (PE).

The present invention further relates to a quantitative, competitive immunoassay which utilizes Luminex Laboratory Multiple Analyte profiling LabMAP® technology (Luminex Corp., Austin Tex.) to evaluate HPV type-specific antibody titers to a plurality of native HPV VLP types. This competitive immunoassay is based on the process of HPV type-specific antibodies in patient sera inhibiting the binding of fluorescently labeled, HPV type-specific, neutralizing detection mAbs. The fluorescent signal from the bound HPV-specific, detection mAbs is inversely proportional to the patients neutralizing antibody titer. Results reflect titers of Ab capable of preventing mAb binding to conformationally sensitive, type-specific, neutralizing epitopes on the respective VLPs.

The LabMAP® (Luminex Corp.; Austin, Tex.) system utilizes microspheres that are 5.6 μm in diameter and composed of polystyrene, divinyl benzene and methacrylic acid. The LabMAP® microspheres are carboxylated to allow for covalent attachment of proteins, polysaccharides or nucleic acids. As used herein, LabMAP microspheres are covalently attached to HPV VLPs. Internally, LabMAP microspheres contain different proportions of red and infra-red emitting fluorochromes, allowing 100 spectrally addressable microsphere sets to be obtained, which are commercially available form the Luminex Corp. (Austin, Tex.).

One of skill in the art will recognize that in addition to the LabMAP® system, other systems comprising sets of spectrally addressable microspheres can be used in the methods of the present invention. Such systems can be developed using unique proportions of two or more fluorescent dyes to define a microsphere set. Methods for developing spectrally addressable bead sets are known in the art. See, e.g., WO 99/19515, and U.S. Pat. No. 5,723,218. In addition, fluorescent beads may be purchased commercially from a number of vendors including, but not limited to, Bangs Laboratories, Inc. (Fishers, Ind.), Dynal Particles AS (Oslo, Norway), and Polymer Laboratories (Amherst, Mass.).

In one embodiment of the present invention, HPV type-specific antibody responses to a plurality of HPV types are detected simultaneously by analyzing the fluorescent signal associated with the different microspheres that have distinct spectral properties. The unique spectral addresses of the microsphere sets allow the different microsphere sets to be distinguished from each other.

The fluorescence emitted by the mAbs coupled to specific fluorescent reporters can be detected by a flow cytometer or other detection instrument that is capable of both distinguishing between the unique characteristics defining a plurality of microsphere sets and detecting the fluorescence of the fluorescent detection antibody. Where fluorescent reporter molecules are used in conjunction with the methods of the present invention to quantify the HPV VLPs at the surface of the beads, the detection instrument should comprise a method of exciting the reporter molecule coupled to the detection antibody. Where one of skill in the art chooses to use microsphere sets that are distinguished by a unique spectral property, the detection instrument should further comprise a method of distinguishing the spectral properties. For example, microsphere sets that are distinguished based on unique spectral properties may consist of distinguishing proportions of two or more fluorescent dyes. In such a case, the detection instrument should comprise a means for exciting the fluorescent dyes within the microspheres. Means for exciting fluorescent dyes include, but are not limited to, argon and krypton ion lasers, helium-neon lasers, helium cadmium lasers, diode lasers and solid-state lasers such as neodynium-YAG lasers.

An exemplary detection instrument of the present invention is a flow cytometer. Flow cytometry is a laser-based technology that is used to measure characteristics of biological particles. The underlying principle of flow cytometry is that light is scattered and fluorescence is emitted as light from the excitation source strikes the moving particles. This technology, when used in conjunction with the methods of the present invention, allows microsphere sets to be distinguished based on spectral properties of the beads. Additionally, it allows the presence of HPV-specific antibodies specific to a plurality of HPV types of interest within a subject sample to de detected and quantified.

Automated flow cytometers for distinguishing bead sets and for measuring fluorescence emitted by fluorescent reporter molecules for use as detectable tags bound to the detection antibodies are known in the art and can be adapted for use in this specific assay. Flow cytometers for use in the methods of the present invention are available commercially from several companies including The Luminex Corporation (Austin, Tex.; e.g. the LUMINEX100™), Becton Dickinson (San Jose, Calif.; e.g. FACSCalibur and FACScan cytometers,), Beckman Coulter (Fullerton, Calif.) and Partec GmbH (Münster, Germany).

In a preferred embodiment of the methods of the present invention, a LUMINEX100™ bench-top analyzer is used to acquire data (Luminex Corp.; Austin, Tex.). This instrument combines analysis software with conventional flow cytometry and is designed specifically for use with LabMAP® technology offered by the Luminex Corp. The Luminex instrument fluidics delivers microspheres in a single file through a flow cell, where the microspheres are excited by a red laser and a green laser. The red laser excites the fluorochromes inside the microsphere and the green laser excites the reporter fluorochrome, which quantifies the assay at the beads surface.

Photodiodes and a photomultiplier tube receive fluorescent signals from the microspheres. The Luminex analyzer digitizes the waveforms and delivers the signals to a digital signal processor, which converts the fluorescent signals into fluorescent intensity units. LabMAP® technology, in conjunction with the Luminex analyzer, allows the simultaneous detection of up to 100 distinct assays within the same well.

The assay of the present invention can be performed with or without a wash step. The wash step is performed after the VLP-microspheres, patient sample and labeled detection antibodies have incubated for 2–18 hours and typically consists of 3 washes with 250 μl of PBS/1% BSA. No-wash particle-based flow cytometry assays may advantageously be performed more quickly than assays including a wash step, but may compromise sensitivity and precision. However, it is also possible that the high concentration of serum in a no-wash assay may clog the detection instrument such as the LUMINEX100® and cause many of the VLP-microspheres to fall outside their specified calibration gates, lengthening the read times to greater than one hour. Accordingly, in a preferred embodiment of the invention, the multiplex competitive immunoassay includes a wash step.

The present invention provides a method for simultaneously detecting antibodies to neutralizing epitopes specific to a plurality of distinct HPV subtypes, thus substantially reducing the amount of time required to analyze a clinical or test sample relative to serially performing individual assays designed to detect antibodies of a single HPV type. The methods of the present invention are, therefore, adaptable to high throughput screening of clinical samples for antibodies specific to a plurality of HPV subtypes. Said methods allow screening for numerous samples simultaneously, e.g. through use of a 96-well plate Luminex assay format, but retain high specificity and accuracy. Advantageously, the 96-well format permits the use of automation, further reducing man-hours necessary to analyze clinical samples for the presence of HPV antibodies. The methods of the present invention can be automated, for example, through the use of a Tecan Genesis liquid handler (TECAN Group Ltd., Durham, N.C.). This system provides the dual benefits of saving time and preventing accidental exposure of laboratory personal to potentially infectious serum.

The present invention also relates to a VLP-microsphere complex comprising a microsphere coupled to an HPV virus-like particle. In a preferred embodiment of the invention, the VLP-microsphere complex further comprises a monoclonal antibody bound to the VLP that is detectably tagged with a fluorescent reporter molecule.

In a preferred embodiment of the instant invention, the HPV VLP type of the microsphere complex is selected from the group consisting of: HPV6, HPV11, HPV16 and HPV18.

All publications mentioned herein are incorporated by reference for the purpose of describing and disclosing the methodologies and materials that are disclosed therein that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Virus-Like Particles (VLPs)

VLPs for HPV types-6, -11, -16 and -18 formed by the expression of the L1 gene in yeast *Saccharomyces cerevisiae* were purified from lysates of *Saccharomyces cerevisiae* as previously described in Hofmann et al., *Virology* 209(2): 506–18 (1995); Hofmann et al., *J. Gen. Virol.* 77(pt 3)(1): 465–68; Neeper et al., *Gene* 180(1–2): 1–6 (1996); and Rossi et al., *Hum. Gene Ther.* 11(8): 1165–76 (2000, and as modified in Cook et al., *Protein Expr. Purif.* 17(3): 477–484 (1999), which are herein incorporated by reference.

EXAMPLE 2

Antibodies

The following antibodies were obtained for the assay: H6.B 10.5, which is specific to HPV-6; mAb 8740 or H11.B2 (Chemicon International, Inc., Temecula, Calif.), which is specific to HPV-11; H16.V5, which is specific to HPV-16; and H18.J4, which is specific to HPV-18 (see Christensen et al., *Virology* 224(2): 477–86 (1996); Christensen et al., *J. Virol.* 64(11): 5678–81 (1990); and Christensen et al., *Virology* 223(1): 174–84 (1996)). Each of these antibodies were previously shown to be HPV type-specific and to bind to neutralizing epitopes (Yeager et al., *Virology* 278(2): 570–77 (2000)). The H6.B10.5, H11.B2, H16.V5, and H18.J4 antibodies were labeled with phycoerythrin (PE) (Chromaprobe, Inc., Aptos, Calif.). For use in the assay, the four PE-tagged mAbs were combined so that the final concentration of each mAb was 2.5 µg/ml for H6.B10.5, 1.0 µg/ml for H11.B2, 1.0 µg/ml for H16.V5, and 1.25 µg/ml for H18.J4.

EXAMPLE 3

Covalent Coupling of HPV VLPs to Luminex Microspheres

HPV VLP vaccines have been shown to induce type-specific, neutralizing antibodies in both humans and animals. However, denatured VLPs fail to elicit neutralizing antibodies, demonstrating that conformationally sensitive epitopes on the VLPs are critical to inducing an effective immune response. Additionally, the conformational integrity of the VLPs is sensitive to reducing conditions, pH and ionic conditions (see McCarthy et al., *J. Virol.* 72(1): 32–41 (1998)).

We used a carbodiide-mediated coupling reaction procedure (see Staros et al., *Anal. Biochem.* 156(1): 220–22 (1986)). To determine whether covalently coupling HPV VLPs to Luminex microspheres via the carbodiimide reaction would alter the conformational integrity of the VLPs, we monitored the stability of the VLP-microspheres stored at 4° C. in different buffers in the presence or absence of 1% BSA. The coefficient of variation (% CV) of 32 replicate median fluorescent intensity (Mp measurements of bound detection mAb to the different VLPs was measured for the different storage conditions over a 6 month period.

Luminex microspheres are fluorescent polystyrene beads approximately 5000 nm in diameter with functional carboxyl groups for covalently attaching proteins. Activation of the carboxylated Luminex microspheres was performed first before coupling the VLPs to their respective microspheres. Microspheres were stored at 4° C., in the dark, at a concentration of $1.25 \times 10^7$ microspheres/mi. The microspheres were brought to room temperature, sonicated for 2 minutes to obtain an equal distribution of microspheres, and aliquoted into 1.5 ml vials (VWR, West Chester, Pa.) at $2.5 \times 10^6$ microspheres per vial. Microspheres were pelleted and re-suspended in 400 µl of 0.1 M sodium phosphate buffer pH 6.2. The carboxylated sites on the surface of the microspheres were activated by adding 50 µl of a 50 mg/ml solution of NHS (N-hydroxysulfosuccinimide) and 50 µl of a 50 mg/ml solution of EDC (1-ethyl-3-(3-dimethylaminopropyl)-carbodiimide hydrochloride). The tubes were sonicated for 2 minutes, wrapped in foil and incubated for 20 minutes at room temperature. Following the activation step, the microspheres were washed once in 500 µl of phosphate buffered saline (PBS) pH 7.4 before the addition of the VLPs.

Coupling of the HPV-VLPs to their respective microspheres was performed after the carboxyl sites on the microspheres were activated. HPV-VLPs for types-6, -11, -16 and -18 were diluted in PBS to a concentration of 12 µg/ml. 500 µl of the VLPs (12 µg/mL) was added to the activated microspheres and vortexed on a low setting for 10–20 seconds to resuspend the microspheres. The VLPs were coupled to the following microspheres: VLP-6 to microsphere #132, VLP-11 to microsphere #153, VLP-16 to microsphere #138 and VLP-18 to microsphere #118. The different mnicrospheres were chosen because of the good spectral resolution between the different microsphere sets.

After addition of the VLPs, vials were wrapped in foil and placed on a rotator for two hours at room temperature. This step allows the VLPs to covalently bind to the microspheres by forming amide bonds with the open carboxylate sites on the microspheres. VLPs coupled to microspheres were washed once with 1 mL of PBS containing 0.05% Tween 20 and resuspended in either histidine buffer (20 mM histidine, 0.5 M NaCl, pH 6.2), Column A buffer (50 mM MOPS, 0.5 M NaCl mM, pH 7.0) or PBS with or without 1% BSA to block any remaining open carboxyl sites on the microspheres. VLP-microspheres ($1.0 \times 10^6$ microspheres/mL) were stored in 1 mL aliquots at 4° C. in light resistant vials.

Results from these studies showed that the conformation of the VLPs was not measurably effected by the coupling reaction and that the VLP-Luminex microspheres were stable for at least 5 months when stored at 4° C. in buffers containing 1% BSA as shown for the representative VLP-16 (FIG. 3). These results demonstrated that L1 VLPs expressed from *Saccharomyces cerevisiae* could safely be coupled to Luminex Microspheres without effecting the type-specific, neutralizing epitopes in L1.

EXAMPLE 4

HPV Tape Specific Antibody Quantitation by Competitive Luminex Assay

To perform the competitive immunoassay, VLP-microspheres of each of the four HPV VLP types were pooled in equal volumes and diluted with histidine buffer to a final concentration of $8.0 \times 10^5$ beads/mL. VLP-microspheres were added to each well of a 96 well, black opaque, microtiter plate (Costar, Coming, N.Y.) in a volume of 25 µl (20,000 VLP-microspheres total, 5,000 VLP-microspheres of each HPV type) per well. An HPV stock standard serum was generated by pooling sera from individual African green monkeys that had been immunized with either HPV VLP-6, -11, or -18 VLPs and serum from a chimpanzee that had been immunized with VLP-16. The 4 different serums had previously been titered in a pseudo-neutralization assay (Yaeger et al., *Virology* 278(2): 570–77 (2000)). The stock concentrations of the pooled sera for the different HPV types were 250 mMU/mL for HPV-6 and 1000 mMU/mL for HPV-11, HPV-16 and HPV-18. A titer of 200 mMU/mL has been shown to neutralize HPV11 in an in vivo athymic, nude mouse transplant model of HPV infection (Brown et al., *J. Infect. Dis.* 184(9): 1183–86 (2001)).

To determine if the individual HPV immunoassays could be multiplexed, we examined the four HPV standard serums singly or pooled together in the immunoassay in single and multiplex format. To generate a 12-point standard curve, which was run in duplicate in both the single (simplex) and multiplex formats, eleven two-fold serial dilutions of the stock standard into HPV-negative normal human serum were made. 50 µl of serum was added to each well in duplicate for the standard curve. A negative control was added in quadruplicate, high and low controls were added in duplicate, and thirty-two patient samples were added in duplicate. Sera and VLP-microspheres were incubated at room temperature for 15 minutes in a foil-covered plate. The combined, PE-tagged, type-specific mAbs were added to each well of the plate in a volume of 25 µl and, thereafter, the serum, VLP-microsphere, and mAbs-PE were mixed 3 times using a multichannel pipette. Plates were re-sealed with foil covers and allowed to incubate overnight at room temperature.

Following incubation, all samples were transferred to a filter plate (Millipore, Bedford, Mass.) pre-wet with PBS. The serum samples were washed 3 times with 200 µl of PBS buffer and the VLP-microspheres were re-suspended in 200 µl of PBS+1% BSA for analysis on the Luminex100™. Samples were analyzed on a Luminex$^{100}$ instrument using the XY plate handler platform in multiplexed acquisition mode with gates set to exclude microsphere multimers. Instrument analysis time was approximately 30 sec per sample.

Figure 4B:
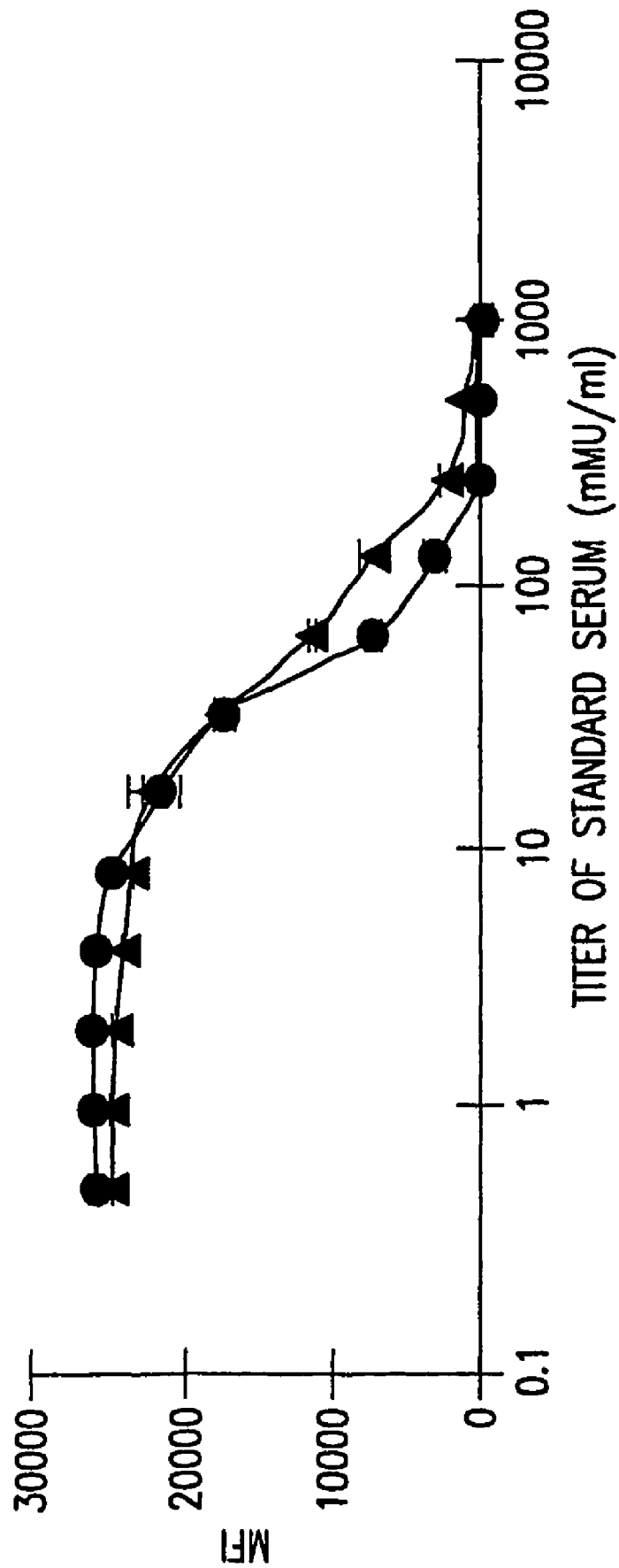
Figure 4C:
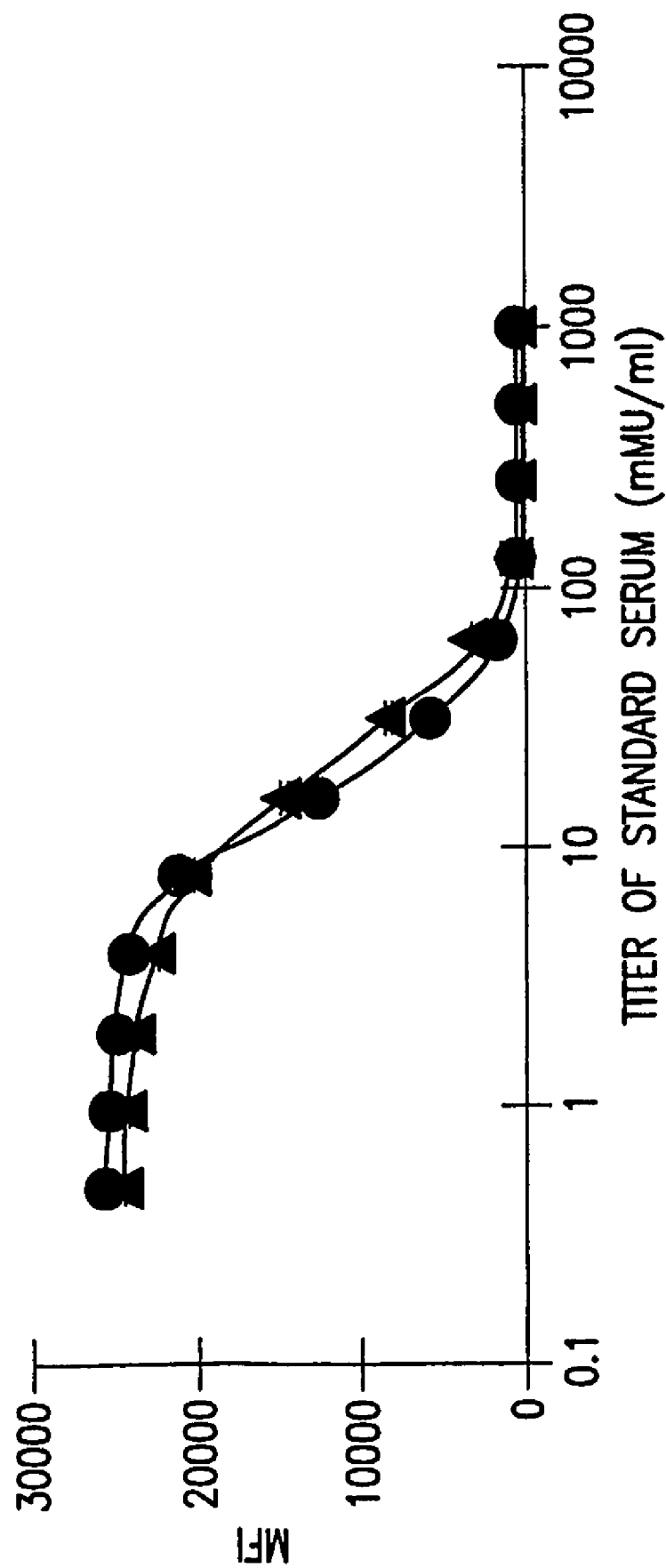
Figure 4D:
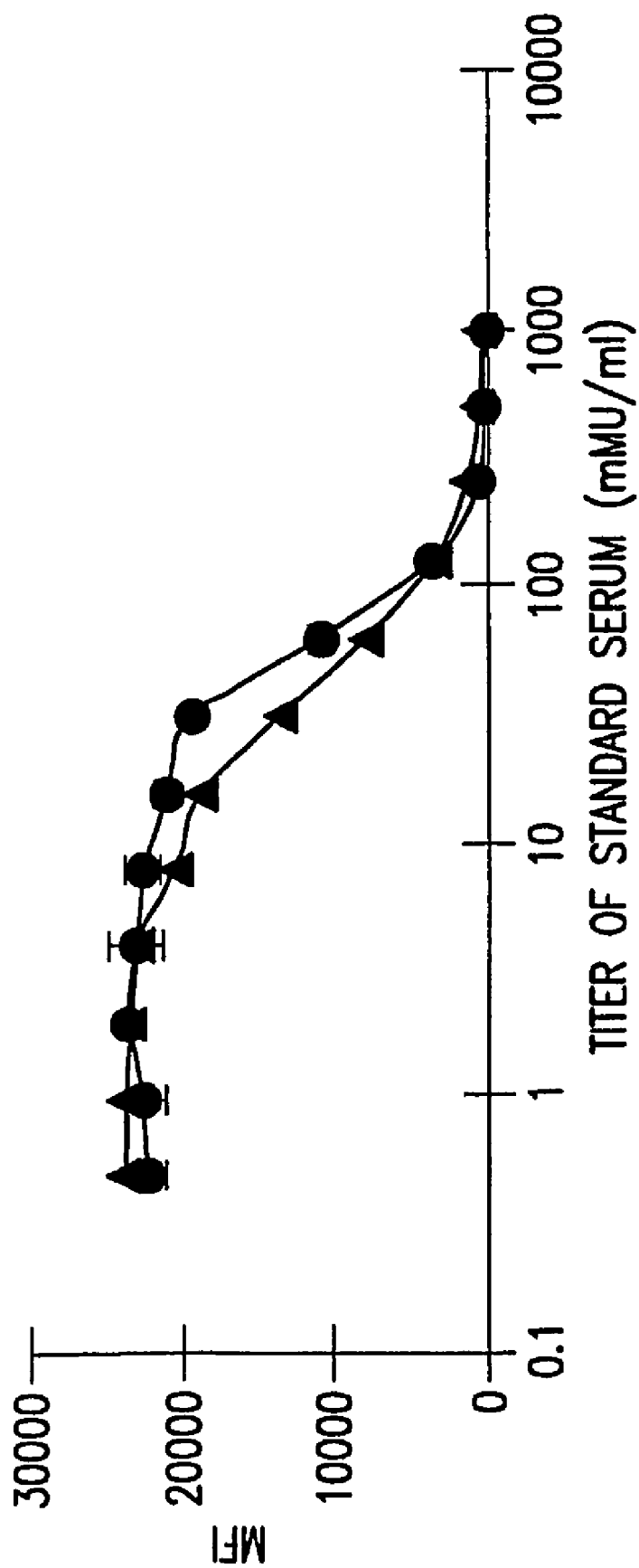

As mentioned, the four mAbs used for detecting HPV Ab responses bind to HPV type-specific epitopes and do not cross-react with the other types. The effect of pooling the four standards together had a minimal effect on the HPV-11, HPV-16 and HPV-18 standard curves (see FIGS. 4B, 4C and 4D). However, multiplexing the assay slightly affected the HPV-6 standard curve (see FIG. 4A). While not wishing to be bound by theory, this effect on the HPV-6 curve was most likely due to the cross-reactivity of the HPV-11 sera onto the HPV-6 VLP. This cross-reactivity was not unexpected, since high titer serum samples from animals or individuals immunized with VLP-11 can neutralize HPV-6 (Yeager et al., *Virology* 278(2): 570–77 (2000)).

The analytical limits of quantitation for the different standard curves in the multiplex assay were determined for HPV-6 (1.2–54.8 mnMU/nL), HPV-11 (9.8–365.6 mMU/mL), HPV-16 (4.5–476.5 mM-U/mL) and HPV-18 (11.3–203.0 mMU/mL), which were comparable to the limits of quantitation determined for the cRIA (see EXAMPLE 7 and FIG. 8).

The precision of the HPV-Luminex immunoassay was determined using eight replicate low, medium and high titer serum samples (data not shown). For within-run precision, the CV ranged from 4.3–4.5% for HPV-6, 3.6–7.4% for HPV-11, 7.4–22.0% for HPV-16 and 2.1–23.9% for HPV-18. Despite the slight affect multiplexing had on the HPV6 standard curve, the HPV Luminex assay of the present invention showed good correlation with the competitive HPV type-specific RIAs (Pearson correlation coefficients between 0.751 and 0.837, see EXAMPLE 7). It is also noted that changing the number of microspheres analyzed did not effect the MFI values (data not shown).

EXAMPLE 5

Effects of Assay Diluents and Washes

We also examined the effect of several different assay diluents on the immunoassay and the effect of adding a filtration-wash step to the procedure. Performing the assay in either a serum or a PBS 1% BSA matrix gave similar results (FIG. 5), suggesting that patient serum could be diluted into a PBS 1% BSA sample diluent for high titer samples. The addition of a filtration-wash step did not significantly affect the standard curves (FIG. 5), but did significantly improve read times from 80–100 minutes per plate to 30–40 minutes per plate. The optimized assay was performed in a serum NHS matrix and the samples were transferred to a filter-plate that was washed 3 times in PBS 1% BSA before being placed on the Luminex100™.

EXAMPLE 6

Data Analysis

Relative inhibition of mAb-PE binding was compared to a standard curve using a four-parameter logistic curve fit (O'Connell et al., American Statistical Association, *Proceedings of the Biopham Section*, p. 180–85 (1992)). The immune reference sera used for the standard curve were assigned arbitrary values expressed in milli-Merck Units (mMU/mL). A neutralizing Ab titer >200 mnMU/mL for HPV-11 has been shown to neutralize ~$10^8$ virions in the athynic mouse xenograft assay (Bryan et al., *J. Med. Virol.* 53(3): 185–88 (1997)). Data in median fluorescent intensity (MFI) units was processed in a Microsoft Excel spreadsheet (Microsoft, Redmond, Wash.). Error bars represent the standard deviation of duplicate measurements. The Pearson correlation coefficient was used when comparing the Luminex Ab titer results with Ab titers obtained in the HPV-cRIA.

EXAMPLE 7

HPV Competitive Radioimmunoassay (cRIA)

To determine the accuracy of the Luminex assay to the currently employed individual cRIA assays, we tested a panel of 45 samples twice in both assay formats. Fifteen negative, 15 low, 10 medium and 5 high titer samples to all 4 HPV types were run in duplicate in both assay formats and the relative concordance of the two assays was determined.

HPV type specific competitive RIAs were used to evaluate HPV type-specific antibody titers to native HPV-6, HPV-11, HPV-16 and HPV-18 VLPs as previously described (Palker et al., *Vaccine* 19(27): 3733–43 (2001)). Briefly, HPV L1 VLP antigens at 100 ng/ml (HPV-6, HPV-11), 50 ng/ml (HPV-16), and 175 ng/ml (HPV-18) were coated onto solid phase polystyrene beads (¼ inch with specular finish, Precision Plastic Ball Co., Franklin Park, Ill.) for 1 h at room temperature (5 beads/ml) with mild agitation. The beads were washed with 50 mM MOPS, 0.5 M NaCl, pH 7.0 and stored submerged at 4° C. in MOPS buffer until further use. Equal volumes of immune sera (100 μl) and diluted mAb sera 1:12,500 for H6.B10.5, 1:160,000 for H11.B2, 1:800,000 for H16.V5 or 1:200,000 for H18.J4 in PBS containing 1% BSA, 0.1% Tween 20 and 0.1% sodium azide were mixed in a well of a 20 well Abbott assay plate. A single HPV VLP-coated bead was added to each well, incubated overnight at RT, washed with deionized water, incubated with $^{125}$I-labeled goat anti-mouse IgG (NFN Life Sciences, Boston, Mass.) at 37° C. for 2.5 h, washed with deionized water and counted in a gamma-counter (Wallac, Turku, Finland). Relative inhibition of mAb binding was compared to a standard reference serum using a four parameter logistic curve fit. The reference sera used had been assigned arbitrary values expressed in milli-Merck Units (mMU/ml).

Figure 6A:
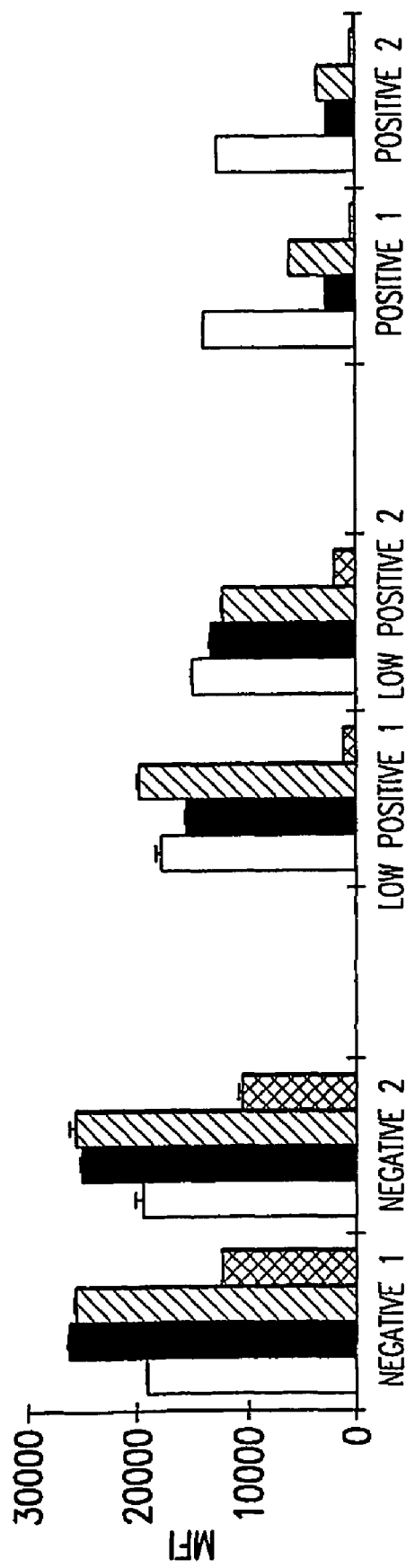
FIG. 6 shows the calculated HPV type-specific, neutralizing antibody titers. Panel A shows the median fluorescence values (MFI) for four representative HPV negative, low-positive and seropositive samples. Results obtained with each representative HPV type are depicted by different colored bars: gray bars represent HPV 6; striped bars represent HPV11; black bars represent HPV16; and white bars represent HPV 18. Panel B shows the antibody titers in Milli-Merck Units per mL (mMU/mL) values for the same four representative samples shown in (A). Error bars represent the standard deviation of duplicate samples.
Figure 6B:
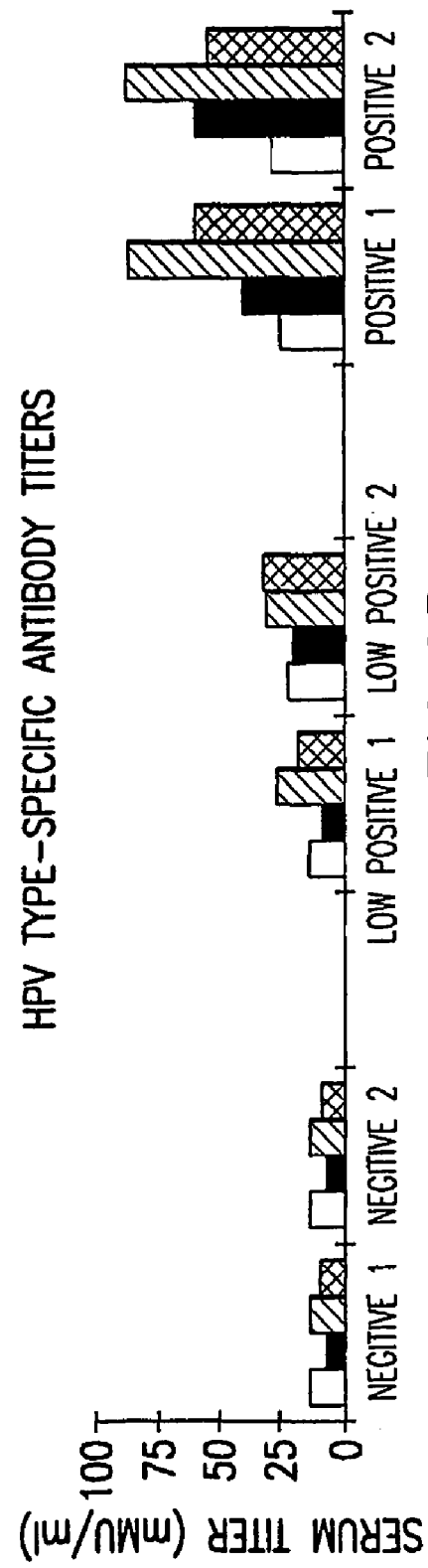

A set of four representative samples that were negative, low positive and positive for antibodies to HPV types-6, -11, -16, and -18, shows the inverse relationship between median fluorescence intensity (MEG (FIG. 6A) and the calculated serum titer (FIG. 6B) in the HPV-Luminex assay. Representative average titers in milli-Merck Units per mL (mMU/mL) for the HPV-16 cRIA and Luminex assays are shown in FIG. 7. Comparing the log titers determined in both assay formats revealed that the two assays showed good concordance. Specifically, the Pearson correlation coefficients (R2) for the two assay formats were all greater than 0.75 (HPV-6, 0.837; HPV-11, 0.751; HPV-16, 0.768; HPV-18, 0.775) suggesting good agreement between the two assay formats. In addition, the HPV Luminex assay had a 0% false positive and a 0% false negative rate when compared to the cRIAs.

What is claimed is:

1. A method for detecting antibodies to neutralizing epitopes on a plurality of human papillomavirus (HPV) types in a sample from a subject comprising:
   (a) providing a plurality of microsphere sets, wherein each of the plurality of microsphere sets comprises:
      a plurality of microsphere complexes, each complex comprising a microsphere coupled to a HPV virus-like particle (VLP) and a type-specific monoclonal antibody (mAb) that binds to the VLP; wherein the mAb is detectably tagged with a fluorescent reporter molecule; and wherein the HPV VLP is of a different HPV type relative to the HPV type of the VLP of a different microsphere set; and
   wherein microspheres of one microsphere set differ from microspheres of another microsphere set in a fluorescence emission property that distinguishes the microspheres of one set from those of another set;
   (b) contacting the plurality of microsphere sets with the sample so that antibodies within the sample can bind to the VLPs; and
   (c) for each microsphere set, determining either
      (i) the amount of detectably tagged monoclonal antibodies that bind to the VLP; or
      (ii) the amount of detectably tagged monoclonal antibodies that do not bind to the VLP;
   (d) comparing the amount obtained in (c) to a control, wherein a reduction in the amount of binding of the detectably tagged monoclonal antibodies to the HPV VLPs indicates that antibodies to HPV neutralizing epitopes are present in the sample of the subject which are specific to that HPV type.

2. The method of claim 1, further comprising the step of quantifying the antibody titre specific to each of the plurality of HPV types in the sample from the subject.

3. The method of claim 1, wherein the plurality of HPV VLPs are of an HPV type selected from the group consisting of: HPV6, HPV11, HPV16, HPV18, HPV31, HPV33, HPV35, HPV39, HPV45, HPV51, HPV52, HPV55, HPV56, HPV58, HPV59, and HPV68.

4. The method of claim 3, wherein the plurality of microsphere sets comprise HPV VLPs of HPV type HPV6, HPV11, HPV16 and HPV18.

5. The method of claim 1, wherein the sample is serum.

6. The method of claim 2, wherein a LUMINEX 100 analyzer is used to determine the amount of detectably tagged monoclonal antibodies that bind to the VLP is reduced relative to the control and to quantify antibody titre.

7. The method of claim 2, wherein a flow cytometer is used to determine if the amount of detectably tagged monoclonal antibodies that bind to the VLP is reduced relative to the control and to quantify antibody titre.

8. The method of claim 1, wherein the type-specific monoclonal antibody is tagged with phycoerythrin.

9. The method of claim 4, wherein the HPV6 VLPs are bound to the mAb H6.B10.5, the HPV11 VLPs are bound to the mAb H11.B2, the HPV16 VLPs are bound to the mAb H16.V5, and the HPV18 VLPs are bound to the mAb H18.J4.

10. A microsphere complex comprising a microsphere coupled to a human papillomavirus (HPV) virus-like particle (VLP).

11. The microsphere complex of claim 10, further comprising a detectably tagged monoclonal antibody bound to the VLP.

12. The microsphere complex of claim 11, wherein the monoclonal antibody is detectably tagged with phycoerythrin.

13. The microsphere complex of claim 11, wherein the HPV VLP type is selected from the group consisting of: HPV6, HPV11, HPV16, and HPV18.

14. A method for detecting antibodies to neutralizing epitopes on human papillomavirus (HPV) types -6, -11, -16 and -18 in a sample from a subject comprising:
(a) providing a first, a second, a third, and a fourth microsphere set, wherein:
  (i) the first microsphere set comprises a plurality of microsphere complexes, each complex comprising a microsphere coupled to an HPV6 virus-like particle (VLP) and a H6.B10.5 monoclonal antibody (mAb) that binds to the VLP; wherein the mAb is labeled with a fluorescent reporter molecule;
  (ii) the second microsphere set comprises a plurality of microsphere complexes, each complex comprising a microsphere coupled to an HPV11 VLP and a H11.B2 mAb that binds to the VLP; wherein the mAb is labeled with a fluorescent reporter molecule;
  (iii) the third microsphere set comprises a plurality of microsphere complexes, each complex comprising a microsphere coupled to an HPV16 VLP and a H16.V5 mAb that binds to the VLP; wherein the mAb is labeled with a fluorescent reporter molecule; and
  (iv) the fourth microsphere set comprises a plurality of microsphere complexes, each complex comprising a microsphere coupled to an HPV18 VLP and a H18.J4 mAb that binds to the VLP; wherein the mAb is labeled with a fluorescent reporter molecule;
and, wherein the microspheres of each microsphere set are labeled with distinguishing proportions of two or more fluorescent dyes, allowing each microsphere set to be distinguished from a different set based on a unique spectral property;
(b) contacting the four microsphere sets with the sample so that antibodies within the sample can bind to the VLPs; and
(c) for each microsphere set, determining the amount of detectably tagged monoclonal antibodies that bind to the VLP; and
(d) comparing the amount obtained in (c) to a control, wherein a reduction in the amount of binding of the monoclonal antibodies to the HPV VLPs indicates that antibodies to HPV neutralizing epitopes are present in the sample of the subject which are specific to HPV6, -11, -16, or 18.

* * * * *